United States Patent
Greene et al.

(10) Patent No.: US 6,391,853 B1
(45) Date of Patent: May 21, 2002

(54) HUMAN TISSUE INHIBITOR OF METALLOPROTEINASE-4

(75) Inventors: John M. Greene, Gaithersburg; Craig A. Rosen, Laytonsville, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/262,087

(22) Filed: Mar. 4, 1999

Related U.S. Application Data

(62) Division of application No. 08/463,261, filed on Jun. 5, 1995, which is a continuation of application No. PCT/US94/14498, filed on Dec. 13, 1994.

(51) Int. Cl.[7] .............................. A61K 38/57; C12N 9/64
(52) U.S. Cl. .......................................... 514/12; 435/226
(58) Field of Search .............................. 514/12; 435/226

(56) References Cited

U.S. PATENT DOCUMENTS

| 5,643,752 A | 7/1997 | Hawkins et al. | 435/69.2 |
| 5,914,392 A | 6/1999 | Hawkins et al. | 530/387.1 |

FOREIGN PATENT DOCUMENTS

| WO | WO 90/11287 | 10/1990 |
| WO | WO 96/18725 | 6/1996 |

OTHER PUBLICATIONS

Kaczorek, M., et al., Molecular Cloning and Synthesis of Biologically Active Human Tissue Inhibitor of Matalloproteinases in Yeast, Bio/Technology 5:595–598 (1987).

Uria, J.A., et al., Structure and Expression in Breast Tumors of Human TIMP–3, a New Member of the Metalloproteinase Inhibitor Family, Cancer Research 54:2091–2094 (1994).

Shimizu, N., et al., Gene Mapping and Fine–Structure Analysis of the Human Genome Using Flow–Sorted Chromosomes, Adv. Tech. Chromosome Res., K. W. Adolph (editor), Dekker, New York, NY, 135–153 (1991).

Rasmussen, H., et al., Matrix Metalloproteinase Inhibition as a Novel Anticancer Strategy: A Review with Special Focus on Batimastat and Marimastat, Pharmacol. Ther. 75:69–75 (1997).

Wang, M., et al., Inhibition of tumor growth and metastatis of human breast cancer cells transfected with tissue inhibitor of metalloproteinase 4, Oncogene 14:2767–2774 (1997).

Dollery, C., et al., TIMP–4 Is Regulated by Vascular Injury in Rats, Ann. N.Y. Acad. Sci. 878:740–741 (1999).

Thomas, P., et al., Differential expression of matrix metalloproteinases and their inhibitors in non–small cell lung cancer, J. Pathol. 190:150–156 (2000).

Liu, Y., et al., Preparation and Characterization of Recombinant Tissue Inhibitor of Metalloproteinase 4 (TIMP–4), J. Biol. Chem., 272:20479–20483 (1997).

Dollery, C., et al., TIMP–4 Is Regulated by Vascular Injury in Rats, Circ. Res. 84(5):498–504 (1999).

Stracke, J., et al., Biochemical Characterization of the Catalytic Domain of Human Matrix Metalloproteinase 19, J. Biol. Chem., 275:14809–14816 (2000).

Bigg, H., et al., Specific, High Affinity Binding of Tissue Inhibitor of Metalloproteinases–4 (TIMP–4) to the COOH–terminal Hemopexin–like Domain of Human Gelatinase A, J. Biol. Chem., 272:15496–15500 (1997).

Toth, M., et al., TIMP–2 Acts Synergistically with Synthetic MMP Inhibitors but not with TIMP–4 to Enhance the MT1–MMP–dependent Activation of Pro–MMP–2, JBC Papers in Press, Manuscript M006871200 (Sep. 20, 2000).

Stetler–Stevenson, W., Matrix metalloproteinases in angiogenisis: a moving target for therapeutic intervention, J. Clinical Investigation 103:1237–1241 (1999).

Nagase, H., Matrix Metalloproteinases J. Biol. Chem., 274:21491–21494 (1999).

Yu, A., et al., Matrix Metalloproteinases Novel Targets for Directed Cancer Therapy, Drugs & Aging 11(3):229–244 (1997).

Hiraoka, N., et al., Matrix Metalloproteinases Regulate Neovascularization by Acting as Pericellular Fibrinolysins, Cell 95:365–377 (1998).

Rosenthal, E., et al., Role of membrane type 1–matrix metalloproteinase and gelatinase A in head and neck squamous cell carcinoma invation in vitro, Otolaryngology–Head and Neck Surgery 121:337–343 (1999).

Tsunezuka, Y., et al., Expression of Membrane–type Matrix Metalloproteinase 1 (MT1–MMP) in Tumor Cells Enhances Pulmonary Metastasis in an Experimental Metastatis Assay, Cancer Research 56:5678–5683 (1996).

Kadono, Y., et al., Transformation of Epithelial Madin–Darby Canine Kidney Cells with p60[v–src] Induces Expression of Membrane–Type 1 Matrix Metalloproteinase and Invasiveness, Cancer Research 58:2240–2244 (1998).

Hotary, K., et al., Regulation of Cell Invasion and Morphogenesis in a Three–dimensional Type I Collagen Matrix by Membrane–type Matrix Metalloproteinases 1, 2, and 3, J. Cell Biology 149:1309–1323 (2000).

*Primary Examiner*—Rebecca E. Prouty
(74) *Attorney, Agent, or Firm*—Human Genome Sciences, Inc.

(57) ABSTRACT

A human tissue inhibitor of metalloproteinases-4 polypeptide and DNA (RNA) encoding such polypeptide and a procedure for producing such polypeptide by recombinant techniques. Also disclosed are methods for utilizing such polypeptide for the treatment of diseases, including arthritis and cancer. Antagonists against such polypeptides and their use as a therapeutic to resorb scar tissue are also disclosed. Diagnostic assays for detecting levels of human TIMP-4 protein and mutations in human TIMP-4 nucleic acid sequence are also disclosed.

106 Claims, 3 Drawing Sheets

Figure 1A

```
  1  ATGCCTGGGAGCCCTCGGCCCGGCCAAGCTGGGTGCTGTTGCTGCGGCTGCTGGCGTTG    60
  1   M  P  G  S  P  R  P  A  P  S  W  V  L  L  L  L  R  L  L  A  L    20

61  CTGCGGCCCCCCGGGGGCTGGGTGAGGCATGCAGCTGCGCCGGCCACCCTCAGCAGCAC   120
 21   L  R  P  P  G  L  G  E  A  C  S  C  A  P  A  H  P  Q  Q  H    40

121  ATCTGCCACTCGGCACTTGTGATTCGGGCCAAAATCTCCAGTGAGAAGGTAGTTCCGGCC   180
 41   I  C  H  S  A  L  V  I  R  A  K  I  S  S  E  K  V  V  P  A    60

181  AGTGCAGACCCTGCTGACACTGAAAAAATGCTCCGGTATGAAATCAAACAGATAAAGATG   240
 61   S  A  D  P  A  D  T  E  K  M  L  R  Y  E  I  K  Q  I  K  M    80

241  TTTCAAAGGGTTTGAGAAAGTCAAGGATGTTCAGTATATCTATACGCCTTTTGACTCTTCC   300
 81   F  K  G  F  E  K  V  K  D  V  Q  Y  I  Y  T  P  F  D  S  S   100

301  CTCTGTGGTGTGAAACTAGAAGCCAACAGCCAGAAGCAGTATCTCTTGACTGGTCAGGTC   360
101   L  C  G  V  K  L  E  A  N  S  Q  K  Q  Y  L  L  T  G  Q  V   120
```

Figure 1B

```
361  CTCAGTGATGGAAAAGTCTTCATCCATCTGTGCAACTACATCGAGCCCTGGGAGGACCTG  420
121   L  S  D  G  K  V  F  I  H  L  C  N  Y  I  E  P  W  E  D  L   140

421  TCCTTGGTGCAGAGGGAAAGTCTGAATCATCATTACCATCTGAACTGTGGCTGCCAAATC  480
141   S  L  V  Q  R  E  S  L  N  H  H  Y  H  L  N  C  G  C  Q  I   160

481  ACCACCTGCTACACAGTACCCTGTACCATCTCGGCCCCTAACGAGTGCCTCTGGACAGAC  540
161   T  T  C  Y  T  V  P  C  T  I  S  A  P  N  E  C  L  W  T  D   180

541  TGGCTGTTGGAACGAAAGCTCTATGGTTACCAGGCTCAGCATTATGTCTGTATGAAGCAT  600
181   W  L  L  E  R  K  L  Y  G  Y  Q  A  Q  H  Y  V  C  M  K  H   200

601  GTTGACGGGCACCTGCCAGCTGGTACCGGGGCCACCTGCCTCTCAGGAAGGAGTTTGTTGAC  660
201   V  D  G  T  C  S  W  Y  R  G  H  L  P  L  R  K  E  F  V  D   220

661  ATCGTTCAGCCCTAG  675
221   I  V  Q  P  *   225
```

HUMAN TISSUE INHIBITOR OF METALLOPROTEINASE-4

This application is a Divisional of and claims priority under 35 U.S.C. section 120 to patent application Ser. No. 08/463,261, filed Jun. 5, 1995, pending, which is a continuation U.S. patent application Ser. No. PCT US94/14498 filed Dec. 13, 1994, both of which are incorporated herein by reference in their entireties.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human tissue inhibitor of metalloproteinase-4 polypeptides, hereinafter referred to as "human TIMP-4". The invention also relates to inhibiting the action of such polypeptides.

The extracellular matrix is a complex structure that contains collagen, proteoglycan, glycosaminoglycan, glycoproteins (fibronectin, chondronectin, laminin) and in some tissues, elastin (Hay, E. D., *J. Cell Biol.,* 91:205–223 (1981)).

Matrix metalloproteinases (MMP's) constitute the major group of zinc-binding endopeptidases that degrade extracellular matrix proteins, for example connective tissue, collagen and gelatin, during remodeling of connective tissue during normal physiological and some pathological processes. The unrestrained activity of MMP's may result in extensive tissue damage, and these enzymes have been implicated in a variety of disease processes, including tumor cell invasion, tumor angiogenesis and rheumatoid arthritis (Okada, Y., et al., *J. Biol. Chem.,* 261:14245–14255 (1986)). The MMP's are secreted from cells as inactive zymogens and their activity in the extracellular environment is regulated by various activators and inhibitors (Matrisian, L. M., *Trends Genet.,* 6:121–125 (1990)).

Regulation of metalloproteinase-mediated proteolysis may occur by naturally occurring inhibitor proteins, such as tissue inhibitor of metalloproteinase (TIMP). The balance between the production and activation of the MMP's, and their inhibition by natural inhibitors such as TIMP, determines, in both physiological and pathological conditions, whether connective tissue is degraded.

MMP's include a number of proteases, exemplified by interstitial (type I) collagenase itself, the stromelysins (also known as proteoglycanases or transins), fibroblast and polymorphonuclear leukocyte gelatinases (also known as collagen-IV-ases), and 'pump-1' (putative metalloproteases 1, uterine metalloproteases) [Goldberg et al, J. Biol. Chem. 2610:6600 (1986); Whitham et al, Biochem. J. 240:913 (1986); Breathnach et al, Nucleic Acids Res., 15:1139 (1987); Muller et al, Biochem. J., 253:187 (1988); Collier et al, J. Biol. Chem., 263:6579 (1988); Murphy et al, Biochem. J., 258:463 (1989); Quantin et al, Biochem. (N.Y.), 28:5327 (1989); Birkedal-Hansen, J. Oral Pathol., 17:445 (1988)].

In general, the mammalian family of proteases has one or more of the following properties: (a) optimal proteolytic activity around neutral pH; (b) dependence of the enzyme's activity on the presence of zinc, as evident by the loss of activity on treatment with divalent metal ion chelators, such as 1.10 phenanthroline (preferential chelation of zinc), or EDTA (less restricted chelating properties; EDTA and EGTA also contribute to enzyme inactivation via chelation of calcium ions required for enzyme stability); (c) inhibition by TIMPs; (d) absence of significant inhibition by known inhibitors of other families of neutral, zinc-containing metalloproteases, such as thermolysis, angiotensin-converting enzyme and 'enkephalinases'; and (e) biosynthesis and secretion as latent precursor forms (zymogens), requiring extracellular activation. Activation has been achieved by a number of endoproteases, organomercurials and chaotropic agents.

In general, members of the family of neutral metalloprotease enzymes have distinctive substrate specificities. Thus, collagenase type I is unique in its ability to cleave a specific peptide bond within the natural fibrils of the interstitial collagens (e.g. types I, II and III). The gelatinases are only poorly active on these collagens, but are able to degrade denatured interstitial collagens, as well as the non-fibrillar collagens, e.g. type IV, such as are found in the basement membrane. Pump 1 has been reported to act preferentially on denatured collagens (gelatins), though its profile differs from that of the stromelysins or the collagenases type IV. Both the stromelysins and the gelatinases are also capable of degrading non-collagenous structural proteins, such as the core protein of proteoglycan and elastin. Macromolecules involved in cell-to-substratum and cell-to-cell interactions, such as laminin and fibronectin, are also susceptible to degradation by several of these metalloproteases.

Enzymes of this family are produced by synovial and skin fibroblasts, chondrocytes, peripheral mononuclear cells, keratinocytes and gingival tissue, as well as existing within granule storage vesicles in polymorphonuclear leukocytes (PMNLs).

Current information suggests that there is a family of metalloproteinase inhibitors which comprises TIMP-1 (tissue inhibitor of metalloproteinases-1); TIMP-2; human TIMP-3 which has been cloned, expressed and mapped to human chromosome 22; and chicken tissue inhibitor of metalloproteinase (ChIMP-5). The polypeptide of the present invention has been putatively identified as a novel human TIMP polypeptide based on amino acid sequence homology.

In accordance with one aspect of the present invention, there is provided a novel mature polypeptide which is human TIMP-4, as well as biologically active and diagnostically or therapeutically useful fragments, analogs and derivatives thereof.

In accordance with another aspect of the present invention, there are provided isolated nucleic acid molecules encoding human TIMP-4, including mRNA's, DNA's, cDNA's, genomic DNA as well as biologically active and diagnostically or therapeutically useful fragments, analogs and derivatives thereof.

In accordance with yet a further aspect of the present invention, there is provided a process for producing such polypeptide by recombinant techniques which comprises culturing recombinant prokaryotic and/or eukaryotic host cells, containing a human TIMP-4 nucleic acid sequence under conditions promoting expression of protein and subsequent recovery of said protein.

In accordance with yet a further aspect of the present invention, there is provided a method for treating conditions which are related to insufficient human TIMP-4 activity which comprises administering to a patient in need thereof a pharmaceutical composition containing the human TIMP-4 protein of the invention which is effective to supplement a patient's endogenous human TIMP-4 and thereby alleviate said conditions which include, for example, arthritic diseases such as rheumatoid and osteoarthritis, soft tissue rheumatism, polychondritis and tendonitis; bone resorption diseases, such as osteoporosis, Paget's disease, hyperparathyroidism and cholesteatoma; the enhanced collagen destruction that occurs in association with diabetes; the recessive classes of dystrophic epidermolysis bullosa; periodontal disease, alveolitis and related consequences of gingival production of collagenase; corneal ulceration; ulceration of the skin and gastro-intestinal tract and abnormal wound healing; post-operative conditions in which collagenase levels are raised; cancer by blocking the destruction of tissue basement membranes leading to cancer metastasis; demyelinating diseases of the central and peripheral nervous systems; asthma; glomerulosclerosis; septic shock and infection; and psoriasis.

In accordance with yet a further aspect of the present invention, there is provided an antibody against such polypeptides.

In accordance with yet another aspect of the present invention, there are provided nucleic acid probes comprising nucleic acid molecules of sufficient length to specifically hybridize to human TIMP-4 sequences.

In accordance with yet another aspect of the present invention, there are provided antagonists to such polypeptides which may be employed for therapeutic purposes, for example, for remodeling and repairing tissue and for destruction of scar tissue.

In accordance with another aspect of the present invention, there are provided diagnostic assays for detecting diseases related to mutations in human TIMP-4 sequences and over-expression of the polypeptide.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1B shows the cDNA sequence and corresponding deduced amino acid sequence of the full-length human TIMP-4 polypeptide. The standard one-letter abbreviations for amino acids are used. Sequencing was performed using a 373 Automated DNA sequencer (Applied Biosystems, Inc.). Sequencing accuracy is predicted to be greater than 97% accurate.

Figure 2:
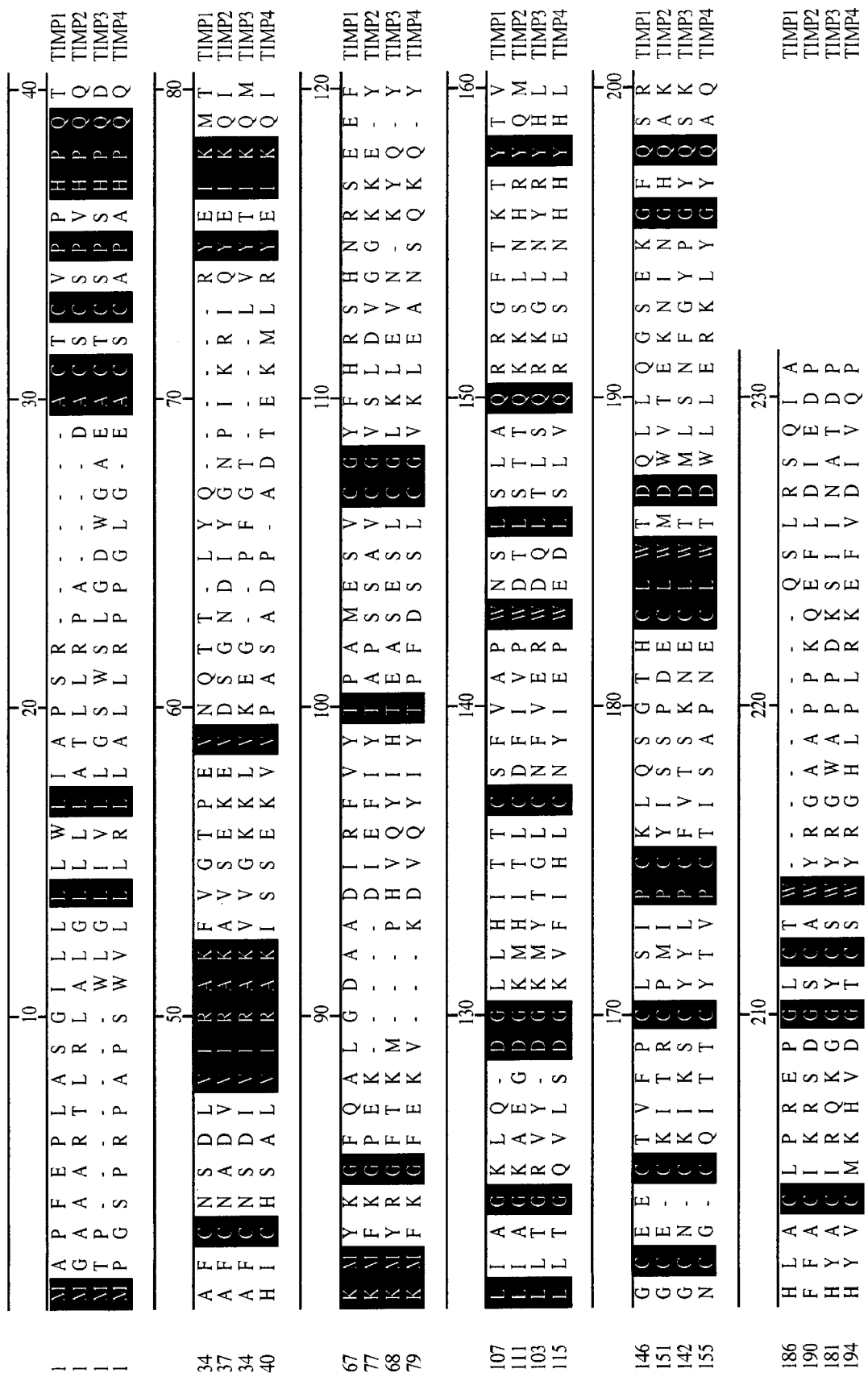
FIG. 2 is an amino acid sequence comparison between the polypeptide of the present invention and other human TIMP polypeptides.

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 75946 on Nov. 11, 1994. The ATCC (American Type Culture Collection) is located at 10801 University Boulevard, Manassas, Va. 20110-2209.

A polynucleotide encoding a polypeptide encodes a protein of 224 amino acid residues of which approximately the first 29 residues represent the leader sequence such that the mature protein comprises 195 amino acid residues. The polynucleotide was discovered in an early stage human brain cDNA library. The protein exhibits the highest degree of homology to Human TIMP-2 with 48% identity and 72% similarity over a 136 amino acid stretch. Human TIMP-4 has the signature 12 cysteine amino acids. The 12 cysteine residues are involved in forming disulfide bonds which are critical for folding into proper tertiary structure. Further, the putative active site is the first 22 amino acid residues past the signal peptide which contains $HIS_7$ and $GLN^9$.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1B or that of the deposited clone or may be a different coding sequence which coding sequence, as a result of the redundancy or degeneracy of the genetic code, encodes the same, mature polypeptide as the DNA of FIGS. 1A–1B or the deposited cDNA.

The polynucleotide which encodes for the mature polypeptide of FIGS. 1A–1B or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1B or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1B or the same mature polypeptide encoded by the cDNA of the deposited clone as well as variants of such polynucleotides which variants encode for a fragment, derivative or analog of the polypeptide of FIGS. 1A–1B or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1B or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1B (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human TIMP-4 polypeptide which has the deduced amino acid sequence of FIGS. 1A–1B or which has the amino acid sequence encoded by the deposited cDNA, as well as fragments, analogs and derivatives of such polypeptide.

The terms "fragment", "derivative" and "analog" when referring to the polypeptide of FIGS. 1A–1B or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1B or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the human TIMP-4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ Coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli$, Streptomyces, *Salmonella typhimurium*; fungal cells, such as yeast; insect cells such as Drosophila S2 and Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNHG16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacz, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), $\alpha$-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include $E.$ $coli,$ $Bacillus$ $subtilis,$ $Salmonella$ $tyhimurium$ and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The human TIMP-4 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The present invention is also directed, in part, to human TIMP-4 which has, as a defining characteristic, the ability to inhibit the action of MMP's. The human TIMP-4 polypeptide may be employed as a metalloproteinase inhibitor to prevent tumor invasion and angiogeneses and subsequent metastases. The human TIMP-4 polypeptide may also be employed to treat arthritic diseases, such as rheumatoid arthritis and osteoarthritis, soft tissue rheumatism, polychondritis and tendonitis; and bone resorption diseases, such as osteoporosis, Paget's disease, hyperparathyroidism and cholesteatoma. Human TIMP-4 may also be employed to prevent enhanced collagen destruction that occurs in association with diabetes, the recessive classes of dystrophic epidermolysis bullosa, periodontal disease and related consequences of gingival production of collagenase. human TIMP-4 may also be employed to inhibit PMNL collagenase release following cellular infiltration to inflamed gingiva, including combatting the greater susceptibility of diabetes patients to periodontal disease.

Human TIMP-4 may also be employed to treat corneal ulceration, for example, that induced by alkali or other burns, by radiation, by Vitamin E or retinoid deficiency; ulceration of the skin and gastro-intestinal tract, and abnormal wound healing, and post-operative conditions including colonic anastomosis, in which collagenase levels are raised.

MMP's mediate tumor growth in situ. Accordingly, human TIMP-4 may be used to block the destruction of cellular basement membranes, which is the mechanism by which cancer cells metastasize. MMP's have been implicated in neovascularization required to support tumor growth and survival, in the tissue remodeling required to accommodate the growing primary and secondary tumors, and in the penetration of tumor cells through the basement membranes of the vascular walls during metastasis.

MMP's are responsible for localized degradation of the follicular wall during ovulation and localized degradation of the, uterine wall for blastocyte implantation. Accordingly, human TIMP-4 may be employed as a contraceptive.

Human TIMP-4 may also be employed as a general growth factor to treat restenosis and similar diseases. Human TIMP-4 may be employed particularly as a growth factor for erythroid cell lineages.

Among the other diseases which human TIMP-4 may be employed to treat includes alveolitis, asthma, psoriasis, glomerulosclerosis, and septic shock since MMP's are involved in the tissue invasiveness of some parasites.

Fragments of the full length human TIMP-4 gene may be used as a hybridization probe for a cDNA library to isolate the full length gene and to isolate other genes which have a high sequence similarity to the gene or similar biological activity. Probes of this type can be, for example, between 20 and 2000 bases. Preferably, however, the probes have between 30 and 50 base pairs. The probe may also be used to identify a cDNA clone corresponding to a full length transcript and a genomic clone or clones that contain the complete human TIMP-4 gene including regulatory and promotor regions, exons, and introns. An example of a screen comprises isolating the coding region of the human TIMP-4 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention is also related to the use of the human TIMP-4 gene as part of a diagnostic assay for detecting diseases or susceptibility to diseases related to the presence of mutated human TIMP-4.

Individuals carrying mutations in the human TIMP-4 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding human TIMP-4 can be used to identify and analyze human TIMP-4 mutations. For example, deletions and tn insertions can be detected by a change in size of the amplified product in comparison to the normal genotype. Point mutations can be identified by hybridizing amplified DNA to radiolabeled human TIMP-4 RNA or alternatively, radiolabeled human TIMP-4 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RPLP)) and Southern blotting of genomic DNA.

In addition to more conventional gel-electrophoresis and DNA sequencing, mutations can also be detected by in situ analysis.

The present invention also relates to a diagnostic assay for detecting altered levels of human TIMP-4 protein in various tissues since an over-expression of the proteins compared to normal control tissue samples may detect the presence of a disease or susceptibility to a disease regulated by human TIMP-4. Assays used to detect levels of human TIMP-4 protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the human TIMP-4 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any human TIMP-4 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to human TIMP-4. Unattached reporter antibody is then washed out. Peroxidase substrates are then added to the dish and the amount of color developed in a given time period is a measurement of the amount of human TIMP-4 protein present in a given volume of patient sample when compared against a standard curve.

A competition assay may be employed wherein antibodies specific to human TIMP-4 are attached to a solid support and labeled human TIMP-4 and a sample derived from the host are passed over the solid support and the amount of label detected, for example by liquid scintillation chromatography, can be correlated to a quantity of human TIMP-4 in the sample.

A "sandwich" assay is similar to an ELISA assay. In a "sandwich" assay human TIMP-4 is passed over a solid support and binds to antibody attached to a solid support. A second antibody is then bound to the human TIMP-4. A third antibody which is labeled and specific to the second antibody is then passed over the solid support and binds to the second antibody and an amount can then be quantitated.

This invention also provides a method of screening compounds to identify those which are agonists or antagonists to be human TIMP-4 polypeptide. An example of such a method comprises obtaining mammalian tissue comprising an extra-cellular matrix, for example, bovine radiocarpal joints. The articular cartilage is cut into smaller disks and labeled with $^{35}$S-sodium sulfate (10 micro Ci/ml) in DMEM for a sufficient time for the cartilage to incorporate the labeled Sodium sulfate. An MMP, for example, stromelysin, or IL1 or TNF is then added to the cartilage disks under appropriate conditions such that tissue breakdown would normally occur. Human TIMP-4 and the compounds to be screened are then added to the reaction mixture for a sufficient time for the MMP to normally break down the cartilage disks. The supernatant, which is the media outside the cartilage disks, is then collected and radioactivity is counted by a liquid scintillation counter. The percentage of $^{35}$S released into the media is then calculated. This release of $^{35}$S-GAG is representative of the proteoglycan pool in the extracellular matrix of cartilage, and reflects proteoglycan degradation by the MMP. The amount of $^{35}$S-GAG, as determined by liquid scintillation chromatography, is then compared to a control assay done in the absence of the compound to be screened and the ability of the compound to agonize or antagonize the action of human TIMP-4 may then be determined.

Examples of potential human TIMP-4 antagonists, in addition to those identified above, include an antibody, or in some cases, an oligonucleotide, which binds to the polypeptide. Alternatively, a potential antagonist may be a mutated form of human TIMP-4, which recognizes natural substrates, but is inactive, and thereby prevent the action of human TIMP-4.

Potential human TIMP-4 antagonists also include antisense constructs prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of human TIMP-4. The antisense RNA oligonucleotide hybridizes to the mRNA in vivo and blocks translation of the mRNA molecule into the human TIMP-4 (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of human TIMP-4.

Another potential human TIMP-4 antagonist is a small molecule which binds to and occupies the active site of the human TIMP-4 thereby preventing human TIMP-4 from interacting with MMP's such that normal biological activity is prevented. Examples of small molecules include but are not limited to small peptides or peptide-like molecules, for example a peptide-bonded molecule.

The human TIMP-4 antagonists may be employed for tissue repair and remodeling, for example, where destruction of scar tissue is desired. In some situations, enhanced connective tissue turnover or remodeling may be desirable, e.g. in resorption of scar tissue; in uterine involution postpartum; in remodeling of fibrotic deposits in the lung, liver or joints. To appropriately control turnover of extra-cellular matrix proteins in these situations would require a balance between the MMP's and human TIMP-4 to appropriately control degradation.

The polypeptides and agonists or antagonists that are also polypeptides may be employed in accordance with the present invention by expression of such polypeptides in vivo, which is often referred to as "gene therapy."

Thus, for example, cells from a patient may be engineered with a polynucleotide (DNA or RNA) ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include; but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechnicues*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CKV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequencers) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. The polypeptides and agonists or antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intra-articular, intra-tumor, intraperitoneal, intramuscular, subcutaneous, intranasal or intradermal routes. The pharmaceutical compositions are administered in an amount which is effective for treating and/or prophylaxis of the specific indication. In general, the pharmaceutical compositions are administered in an amount of at least about 10 μg/kg body weight and in most cases they will be administered in an amount not in excess of about 8 mg/Kg body weight per day and preferably the dosage is from about 10 μg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were. used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of human TIMP-4

The DNA sequence encoding for human TIMP-4, ATCC #75946, is initially amplified using PCR oligonucleotide primers corresponding to the 5' and sequences of the processed human TIMP-4 protein (minus the signal peptide sequence) and the vector sequences 3' to the TIMP-4 gene. Additional nucleotides corresponding to human TIMP-4 were added to the 5' and 3' sequences respectively. The 5' oligonucleotide primer has the sequence 5' GCCAGAG-GATCCTGCAGCTGCGCCCCGGCGCAC 3' contains a BamH1 restriction enzyme site followed by 21 nucleotides of human TIMP-4 coding sequence starting from the presumed terminal amino acid of the processed protein codon. The 3' sequence 5' CGGCTTCTAGAACTAGGGCTGAAC-GATGTCAAC 3' contains an XbaI site and is followed by 18 nucleotides of human TIMP-4. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance ($Amp^r$), a bacterial origin of replication (ori), an IPTG-regulatable promoter operator (P/O), a ribosome binding site (RBS), a 6-His tag and restriction enzyme sites. pQE-9 was then digested with BamH1 and XbaI. The amplified sequences were ligated into pQE-9 and were inserted in frame with the sequence encoding for the histidine tag and the RBS. The ligation mixture was then used to transform E. coli strain m15/pREP4 available from Qiagen by the procedure described in Sambrook, J. et al., Molecular Cloning: A Laboratory Manual, Cold Spring Laboratory Press, (1989). m15/pREP4 contains multiple copies of the plasmid pREP4, which expresses the lacI repressor and also confers kanamycin resistance ($Kan^r$) . Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 ($O.D.^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized human TIMP-4 was purified from this solution by chromatography on a Nickel-Chelate column under conditions that allow for tight binding by proteins containing the 6-His tag (Hochuli, E. et al., J. Chromatography 411:177–184 (1984). Human TIMP-4 (90% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Expression of Recombinant human TIMP-4 in COS Cells

The expression of human TIMP-4 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire human TIMP-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to the target protein allows easy detection of the recombinant protein with an antibody that recognizes the HA epitope.

The plasmid construction strategy is described as follows:

The DNA sequence ATCC #75946, encoding for human TIMP-4 was constructed by PCR using two primers: the 5' primer 5' GCCAGAGGATCCGCCACCATGCCTGG-GAGCCCTCGGCCC 3' contains a BaMHI site followed by 21 nucleotides of human TIMP-4 coding sequence starting from the initiation codon; the 3' sequence 5' CGGCTCTA-GAATCAAGCGTAGTCTGGGACGTCG-TATGGGTAGGGCTGAACGATG TCAAC 3' contains complementary sequences to an XbaI site, translation stop codon, HA tag and the last 18 nucleotides of the human TIMP-4 coding sequence (not including the stop codon). Therefore, the PCR product contains a BamHI site, human TIMP-4 coding sequence followed by HA tag fused in frame, a translation termination stop codon next to the HA tag, and an XbaI site. The PCR amplified DNA fragment and the vector, pcDNAI/Amp, were digested with BamHI and XbaI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant human TIMP-4, COS cells were transfected with the expression vector by DEAB-DEXTRAN method (J. Sambrook, E. Fritsch, T. Maniatis, Molecular Cloning: A Laboratory Manual, Cold Spring Laboratory Press, (1989)). The expression of the human TIMP-4 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of TIMP-4 Using the Baculovirus Expression System

The DNA sequence encoding the full length TIMP-4 protein, ATCC #75946, was amplified using PCR oligonucleotide primers corresponding to the 5' and 3' sequences of the gene:

The 5' primer has the sequence 5' GCCAGAGGATCCATGCCTGG GAGCCCTCGGCCC 3' and contains a BamHI restriction enzyme site (in bold) just behind the first 21 nucleotides of the TIMP-4 gene (the initiation codon for translation "ATG" is underlined).

The 3' primer has the sequence 5' CGGCTTCTAGAAC-TAGGGCTG AACGATGTCAAC 3' and contains the cleavage site for the restriction endonuclease XbaI and 18 nucleotides complementary to the 3' non-translated sequence of the TIMP-4 gene. The amplified sequences were isolated from a 1% agarose gel using a commercially available kit ("Geneclean," BIO 101 Inc., La Jolla, Calif.). The fragment was then digested with the endonucleases BamHI and XbaI and then purified again on a 1% agarose gel. This fragment is designated F2.

The vector pA2 (modification of pVL941 vector, discussed below) is used for the expression of the TIMP-4 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XbaI. The DNA was then isolated from a 1% agarose gel using the commercially available kit ("Geneclean" BIO 101 Inc., La Jolla, Calif.). This vector DNA is designated V2.

Fragment F2 and the plasmid V2 were ligated with T4 DNA ligase. *E. coli* HB101 cells were then transformed and bacteria identified that contained the plasmid (pBacTIMP-4) with the TIMP-4 gene using the enzymes BamHI and XbaI. The sequence of the cloned fragment was confirmed by DNA sequencing.

5 μg of the plasmid pBacTIMP-4 was co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBacTIMP-4 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses were added to the cells and blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 tells were grown in Grace's medium supplemented with 10% heat-inactivated PBS. The cells were infected with the recombinant baculovirus V-TIMP-4 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 4

Expression Pattern of Human TIMP-4 in Human Tissues

20 µg of total RNA from each of the above tissues was denatured and run on a 1.2% formaldehyde agarose gel and capillary blotted onto a nylon filter overnight. RNA was immobilized on the filter by UV cross-linking. A random primer probe was prepared from the EcoRI-XhoI insert of the partial TIMP-4 nucleic acid sequence and used to probe the blot by overnight hybridization in Church buffer with 100 µg/ml denatured herring sperm DNA as a blocking agent. Washing was performed sequentially with 2×SSC/0.1% SDA and 0.2×SSC/0.1% SDS at 65 degrees Celsius. Size markers were the BRL RNA ladder and 18S and 28S ribosomal RNA bands.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time; fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS) penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

What is claimed is:

1. A method for the treatment of a patient having need of TIMP-4 comprising: administering to the patient a therapeutically effective amount of a polypeptide selected from the group consisting of:
   (a) a polypeptide having the deduced amino acid sequence of SEQ ID NO:2 and fragments thereof;
   (b) a polypeptide comprising amino acid 1 to amino acid 195 of SEQ ID NO:2; and
   (c) a polypeptide encoded by the cDNA of ATCC Deposit No. 75946 and fragments of said polypeptide;
wherein said polypeptide and said fragments inhibit metalloproteinase activity.

2. A method of inhibiting metalloproteinase activity which comprises, contacting a metalloproteinase with an amount of a polypeptide effective to inhibit metalloproteinase activity, wherein said polypeptide has an amino acid sequence selected from the group consisting of:
   (a) at least 30 amino acids of the amino acid sequence shown as residues 1 to 224 of SEQ ID NO:2, wherein said at least 30 amino acids retain metalloproteinase inhibiting activity;
   (b) a fragment of the amino acid sequence shown as residues 1 to 224 of SEQ ID NO:2, wherein said fragment retains metalloproteinase inhibiting activity;
   (c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;

(d) a first amino acid sequence at least 90% identical to a second amino acid sequence shown as residues 30 to 224 in SEQ ID NO:2, wherein said first amino acid sequence retains metalloproteinase inhibiting activity;

(e) at least 30 amino acids of the amino acid sequence of the full-length polypeptide encoded by the human cDNA contained in ATCC Deposit No. 75946, wherein said at least 30 amino acids retain metalloproteinase inhibiting activity; and (f) a fragment of the full-length polypeptide encoded by the human cDNA contained in ATCC Deposit No. 75946, wherein said fragment retains metalloproteinase inhibiting activity.

3. The method of claim 2, wherein said polypeptide comprises amino acid sequence (a).

4. The method of claim 3, wherein said polypeptide comprises the amino acid sequence shown as residues 30 to 224 in SEQ ID NO:2.

5. The method of claim 3, wherein said polypeptide comprises the amino acid sequence shown as residues 2 to 224 in SEQ ID NO:2.

6. The method of claim 3, wherein said polypeptide comprises the amino acid sequence shown as residues 1 to 224 in SEQ ID NO:2.

7. The method of claim 2, wherein said polypeptide comprises amino acid sequence (b).

8. The method of claim 2, wherein said polypeptide comprises amino acid sequence (c).

9. The method of claim 2, wherein said polypeptide comprises amino acid sequence (d).

10. The method of claim 2, wherein said polypeptide comprises amino acid sequence (e).

11. The method of claim 10, wherein said polypeptide comprises the amino acid sequence of the mature polypeptide encoded by the human cDNA contained in ATCC Deposit No. 75946.

12. The method of claim 10, wherein said polypeptide comprises the amino acid sequence of the full-length polypeptide encoded by the human cDNA contained in ATCC Deposit No. 75946, excepting the N-terminal methionine.

13. The method of claim 10, wherein said polypeptide comprises the amino acid sequence of the full-length polypeptide encoded by the human cDNA contained in ATCC Deposit No. 75946.

14. The method of claim 2, wherein said polypeptide comprises amino acid sequence (f).

15. The method of claim 2, wherein said polypeptide comprises a heterologous polypeptide sequence.

16. The method of claim 2, wherein said polypeptide is in a pharmaceutically acceptable carrier.

17. A method of inhibiting the destruction of cellular basement membranes in a patient which comprises, administering to the patient, a therapeutically effective amount of a polypeptide having an amino acid sequence selected from the group consisting of:

(a) at least 30 amino acids of the amino acid sequence shown as residues 1 to 224 of SEQ ID NO:2, wherein said at least 30 amino acids retain metalloproteinase inhibiting activity;

(b) a fragment of the amino acid sequence shown as residues 1 to 224 of SEQ ID NO:2, wherein said fragment retains metalloproteinase inhibiting activity;

(c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;

(d) a first amino acid sequence at least 90% identical to a second amino acid sequence shown as residues 30 to 224 in SEQ ID NO:2, wherein said first amino acid sequence retains metalloproteinase inhibiting activity;

(e) at least 30 amino acids of the amino acid sequence of the full-length polypeptide encoded by the human cDNA contained in ATCC Deposit No. 75946, wherein said at least 30 amino acids retain metalloproteinase inhibiting activity; and (f) a fragment of the full-length polypeptide encoded by the human cDNA contained in ATCC Deposit No. 75946, wherein said fragment retains metalloproteinase inhibiting activity.

18. The method of claim 17, wherein said polypeptide comprises amino acid sequence (a).

19. The method of claim 18, wherein said polypeptide comprises the amino acid sequence shown as residues 30 to 224 in SEQ ID NO:2.

20. The method of claim 18, wherein said polypeptide comprises the amino acid sequence shown as residues 2 to 224 in SEQ ID NO:2.

21. The method of claim 18, wherein said polypeptide comprises the amino acid sequence shown as residues 1 to 224 in SEQ ID NO:2.

22. The method of claim 17, wherein said polypeptide comprises amino acid sequence (b).

23. The method of claim 17, wherein said polypeptide comprises amino acid sequence (c).

24. The method of claim 17, wherein said polypeptide comprises amino acid sequence (d).

25. The method of claim 17, wherein said polypeptide comprises amino acid sequence (e).

26. The method of claim 25, wherein said polypeptide comprises the amino acid sequence of the mature polypeptide encoded by the human cDNA contained in ATCC Deposit No. 75946.

27. The method of claim 25, wherein said polypeptide comprises the amino acid sequence of the full-length polypeptide encoded by the human cDNA contained in ATCC Deposit No. 75946, excepting the N-terminal methionine.

28. The method of claim 25, wherein said polypeptide comprises the amino acid sequence of the full-length polypeptide encoded by the human cDNA contained in ATCC Deposit No. 75946.

29. The method of claim 17, wherein said polypeptide comprises amino acid sequence (f).

30. The method of claim 17, wherein said polypeptide comprises a heterologous polypeptide sequence.

31. The method of claim 17, wherein said polypeptide is in a pharmaceutically acceptable carrier.

32. A method of treating restenosis which comprises, administering to a patient, a therapeutically effective amount of polypeptide having an amino acid sequence selected from the group consisting of:

(a) at least 30 amino acids of the amino acid sequence shown as residues 1 to 224 of SEQ ID NO:2, wherein said at least 30 amino acids retain metalloproteinase inhibiting activity;

(b) a fragment of the amino acid sequence shown as residues 1 to 224 of SEQ ID NO:2, wherein said fragment retains metalloproteinase inhibiting activity;

(c) the amino acid sequence of polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;

(d) a first amino acid sequence at least 90% identical to a second amino acid sequence shown as residues 30 to 224 in SEQ ID NO:2, wherein said first amino acid sequence retains metalloproteinase inhibiting activity;

(e) at least 30 amino acids of the amino acid sequence of the full-length polypeptide encoded by the human cDNA contained in ATCC Deposit No. 75946, wherein said at least 30 amino acids retain metalloproteinase inhibiting activity; and (f) a fragment of the full-length polypeptide encoded by the human cDNA contained in ATCC Deposit No. 75946, wherein said fragment retains metalloproteinase inhibiting activity.

33. The method of claim 32, wherein said polypeptide comprises amino acid sequence (a).

34. The method of claim 33, wherein said polypeptide comprises the amino acid sequence shown as residues 30 to 224 in SEQ ID NO:2.

35. The method of claim 33, wherein said polypeptide comprises the amino acid sequence shown as residues 2 to 224 in SEQ ID NO:2.

36. The method of claim 33, wherein said polypeptide comprises the amino acid sequence shown as residues 1 to 224 in SEQ ID NO:2.

37. The method of claim 32, wherein said polypeptide comprises amino acid sequence (b).

38. The method of claim 32, wherein said polypeptide comprises amino acid sequence (c).

39. The method of claim 32, wherein said polypeptide comprises amino acid sequence (d).

40. The method of claim 32, wherein said polypeptide comprises amino acid sequence (e).

41. The method of claim 40, wherein said polypeptide comprises the amino acid sequence of the mature polypeptide encoded by the human cDNA contained in ATCC Deposit No. 75946.

42. The method of claim 40, wherein said polypeptide comprises the amino acid sequence of the full-length polypeptide encoded by the human cDNA contained in ATCC Deposit No. 75946, excepting the N-terminal methionine.

43. The method of claim 40, wherein said polypeptide comprises the amino acid sequence of the full-length polypeptide encoded by the human cDNA contained in ATCC Deposit No. 75946.

44. The method of claim 32, wherein said polypeptide comprises amino acid sequence (f).

45. The method of claim 32, wherein said polypeptide comprises a heterologous polypeptide sequence.

46. The method of claim 32, wherein said polypeptide is in a pharmaceutically acceptable carrier.

47. A method of treating cancer which comprises, administering to a patient, a therapeutically effective amount of a polypeptide having an amino acid sequence selected from the group consisting of:

(a) at least 30 amino acids of the amino acid sequence shown as residues 1 to 224 of SEQ ID NO:2, wherein said at least 30 amino acids retain metalloproteinase inhibiting activity;

(b) a fragment of the amino acid sequence shown as residues 1 to 224 of SEQ ID NO:2, wherein said fragment retains metalloproteinase inhibiting activity;

(c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;

(d) a first amino acid sequence at least 90% identical to a second amino acid sequence shown as residues 30 to 224 in SEQ ID NO:2, wherein said first amino acid sequence retains metalloproteinase inhibiting activity;

(e) at least 30 amino acids of the amino acid sequence of the full-length polypeptide encoded by the human cDNA contained in ATCC Deposit No. 75946, wherein said at least 30 amino acids retain metalloproteinase inhibiting activity; and (f) a fragment of the full-length polypeptide encoded by the human cDNA contained in ATCC Deposit No. 75946, wherein said fragment retains metalloproteinase inhibiting activity.

48. The method of claim 47, wherein said polypeptide comprises amino acid sequence (a).

49. The method of claim 48, wherein said polypeptide comprises the amino acid sequence shown as residues 30 to 224 in SEQ ID NO:2.

50. The method of claim 48, wherein said polypeptide comprises the amino acid sequence shown as residues 2 to 224 in SEQ ID NO:2.

51. The method of claim 48, wherein said polypeptide comprises the amino acid sequence shown as residues 1 to 224 in SEQ ID NO:2.

52. The method of claim 47, wherein said polypeptide comprises amino acid sequence (b).

53. The method of claim 47, wherein said polypeptide comprises amino acid sequence (c).

54. The method of claim 47, wherein said polypeptide comprises amino acid sequence (d).

55. The method of claim 47, wherein said polypeptide comprises amino acid sequence (e).

56. The method of claim 55, wherein said polypeptide comprises the amino acid sequence of the mature polypeptide encoded by the human cDNA contained in ATCC Deposit No. 75946.

57. The method of claim 55, wherein said polypeptide comprises the amino acid sequence of the full-length polypeptide encoded by the human cDNA contained in ATCC Deposit No. 75946, excepting the N-terminal methionine.

58. The method of claim 55, wherein said polypeptide comprises the amino acid sequence of the full-length polypeptide encoded by the human cDNA contained in ATCC Deposit No. 75946.

59. The method of claim 47, wherein said polypeptide comprises amino acid sequence (f).

60. The method of claim 47, wherein said polypeptide comprises a heterologous polypeptide sequence.

61. The method of claim 47, wherein said polypeptide is in a pharmaceutically acceptable carrier.

62. A method of inhibiting tumor invasion which comprises, administering to a patient, a therapeutically effective amount of a polypeptide having an amino acid sequence selected from the group consisting of:
   (a) at least 30 amino acids of the amino acid sequence shown as residues 1 to 224 of SEQ ID NO:2, wherein said at least 30 amino acids retain metalloproteinase inhibiting activity;
   (b) a fragment of the amino acid sequence shown as residues 1 to 224 of SEQ ID NO:2, wherein said fragment retains metalloproteinase inhibiting activity;
   (c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;
   (d) a first amino acid sequence at least 90% identical to a second amino acid sequence shown as residues 30 to 224 in SEQ ID NO:2, wherein said first amino acid sequence retains metalloproteinase inhibiting activity;
   (e) at least 30 amino acids of the amino acid sequence of the full-length polypeptide encoded by the human cDNA contained in ATCC Deposit No. 75946, wherein said at least 30 amino acids retain metalloproteinase inhibiting activity; and
   (f) a fragment of the full-length polypeptide encoded by the human cDNA contained in ATCC Deposit No. 75946, wherein said fragment retains metalloproteinase inhibiting activity.

63. The method of claim 62, wherein said polypeptide comprises amino acid sequence (a).

64. The method of claim 63, wherein said polypeptide comprises the amino acid sequence shown as residues 30 to 224 in SEQ ID NO:2.

65. The method of claim 63, wherein said polypeptide comprises the amino acid sequence shown as residues 2 to 224 in SEQ ID NO:2.

66. The method of claim 63, wherein said polypeptide comprises the amino acid sequence shown as residues 1 to 224 in SEQ ID NO:2.

67. The method of claim 62, wherein said polypeptide comprises amino acid sequence (b).

68. The method of claim 62, wherein said polypeptide comprises amino acid sequence (c).

69. The method of claim 62, wherein said polypeptide comprises amino acid sequence (d).

70. The method of claim 62, wherein said polypeptide comprises amino acid sequence (e).

71. The method of claim 70, wherein said polypeptide comprises the amino acid sequence of the mature polypeptide encoded by the human cDNA contained in ATCC Deposit No. 75946.

72. The method of claim 70, wherein said polypeptide comprises the amino acid sequence of the full-length polypeptide encoded by the human cDNA contained in ATCC Deposit No. 75946, excepting the N-terminal methionine.

73. The method of claim 70, wherein said polypeptide comprises the amino acid sequence of the full-length polypeptide encoded by the human cDNA contained in ATCC Deposit No. 75946.

74. The method of claim 62, wherein said polypeptide comprises amino acid sequence (f).

75. The method of claim 62, wherein said polypeptide comprises a heterologous polypeptide sequence.

76. The method of claim 62, wherein said polypeptide is in a pharmaceutically acceptable carrier.

77. A method of inhibiting angiogenesis which comprises, administering to a patient, a therapeutically effective amount of a polypeptide having an amino acid sequence selected from the group consisting of:
   (a) at least 30 amino acids of the amino acid sequence shown as residues 1 to 224 of SEQ ID NO:2, wherein said at least 30 amino acids retain metalloproteinase inhibiting activity;
   (b) a fragment of the amino acid sequence shown as residues 1 to 224 of SEQ ID NO:2, wherein said fragment retains metalloproteinase inhibiting activity;
   (c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;
   (d) a first amino acid sequence at least 90% identical to a second amino acid sequence shown as residues 30 to 224 in SEQ ID NO:2, wherein said first amino acid sequence retains metalloproteinase inhibiting activity;
   (e) at least 30 amino acids of the amino acid sequence of the full-length polypeptide encoded by the human cDNA contained in ATCC Deposit No. 75946, wherein said at least 30 amino acids retain metalloproteinase inhibiting activity; and
   (f) a fragment of the full-length polypeptide encoded by the human cDNA contained in ATCC Deposit No. 75946, wherein said fragment retains metalloproteinase inhibiting activity.

78. The method of claim 77, wherein said polypeptide comprises amino acid sequence (a).

79. The method of claim 78, wherein said polypeptide comprises the amino acid sequence shown as residues 30 to 224 in SEQ ID NO:2.

80. The method of claim 78, wherein said polypeptide comprises the amino acid sequence shown as residues 2 to 224 in SEQ ID NO:2.

81. The method of claim 78, wherein said polypeptide comprises the amino acid sequence shown as residues 1 to 224 in SEQ ID NO:2.

82. The method of claim 77, wherein said polypeptide comprises amino acid sequence (b).

83. The method of claim 77, wherein said polypeptide comprises amino acid sequence (c).

84. The method of claim 77, wherein said polypeptide comprises amino acid sequence (d).

85. The method of claim 77, wherein said polypeptide comprises amino acid sequence (e).

86. The method of claim 85, wherein said polypeptide comprises the amino acid sequence of the mature polypeptide encoded by the human cDNA contained in ATCC Deposit No. 75946.

87. The method of claim 85, wherein said polypeptide comprises the amino acid sequence of the full-length polypeptide encoded by the human cDNA contained in ATCC Deposit No. 75946, excepting the N-terminal methionine.

88. The method of claim 85, wherein said polypeptide comprises the amino acid sequence of the full-length polypeptide encoded by the human cDNA contained in ATCC Deposit No. 75946.

89. The method of claim 77, wherein said polypeptide comprises amino acid sequence (f).

90. The method of claim 77, wherein said polypeptide comprises a heterologous polypeptide sequence.

91. The method of claim 77, wherein said polypeptide is in a pharmaceutically acceptable carrier.

92. A method of inhibiting metastasis which comprises, administering to a patient, a therapeutically effective amount of a polypeptide having an amino acid sequence selected from the group consisting of:

(a) at least 30 amino acids of the amino acid sequence shown as residues 1 to 224 of SEQ ID NO:2, wherein said at least 30 amino acids retain metalloproteinase inhibiting activity;

(b) a fragment of the amino acid sequence shown as residues 1 to 224 of SEQ ID NO:2, wherein said fragment retains metalloproteinase inhibiting activity;

(c) the amino acid sequence of a polypeptide which possesses metalloproteinase inhibiting activity wherein said amino acid sequence is encoded by a polynucleotide which hybridizes to a DNA consisting of a sequence complementary to SEQ ID NO:1 when incubated in Church buffer with 100 ug/ml denatured herring sperm DNA as a blocking agent followed by washing sequentially with 2×SSC/0.1% SDS and 0.2× SSC/0.1% SDS at 65° C.;

(d) a first amino acid sequence at least 90% identical to a second amino acid sequence shown as residues 30 to 224 in SEQ ID NO:2, wherein said first amino acid sequence retains metalloproteinase inhibiting activity;

(e) at least 30 amino acids of the amino acid sequence of the full-length polypeptide encoded by the human cDNA contained in ATCC Deposit No. 75946, wherein said at least 30 amino acids retain metalloproteinase inhibiting activity; and (f) a fragment of the full-length polypeptide encoded by the human cDNA contained in ATCC Deposit No. 75946, wherein said fragment retains metalloproteinase inhibiting activity.

93. The method of claim 92, wherein said polypeptide comprises amino acid sequence (a).

94. The method of claim 93, wherein said polypeptide comprises the amino acid sequence shown as residues 30 to 224 in SEQ ID NO:2.

95. The method of claim 93, wherein said polypeptide comprises the amino acid sequence shown as residues 2 to 224 in SEQ ID NO:2.

96. The method of claim 93, wherein said polypeptide comprises the amino acid sequence shown as residues 1 to 224 in SEQ ID NO:2.

97. The method of claim 92, wherein said polypeptide comprises amino acid sequence (b).

98. The method of claim 92, wherein said polypeptide comprises amino acid sequence (c).

99. The method of claim 92, wherein said polypeptide comprises amino acid sequence (d).

100. The method of claim 92, wherein said polypeptide comprises amino acid sequence (e).

101. The method of claim 100, wherein said polypeptide comprises the amino acid sequence of the mature polypeptide encoded by the human cDNA contained in ATCC Deposit No. 75946.

102. The method of claim 100, wherein said polypeptide comprises the amino acid sequence of the full-length polypeptide encoded by the human cDNA contained in ATCC Deposit No. 75946, excepting the N-terminal methionine.

103. The method of claim 100, wherein said polypeptide comprises the amino acid sequence of the full-length polypeptide encoded by the human cDNA contained in ATCC Deposit No. 75946.

104. The method of claim 92, wherein said polypeptide comprises amino acid sequence (f).

105. The method of claim 92, wherein said polypeptide comprises a heterologous polypeptide sequence.

106. The method of claim 92, wherein said polypeptide is in a pharmaceutically acceptable carrier.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 675 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..672

(xi) SEQUENCE DESCRIPTION: SEQ ID NO:1:

```
ATG CCT GGG AGC CCT CGG CCC GCG CCA AGC T GG GTG CTG TTG CTG CGG      48
Met Pro Gly Ser Pro Arg Pro Ala Pro Ser T rp Val Leu Leu Leu Arg
 1               5                  10                  15

CTG CTG GCG TTG CTG CGG CCC CCG GGG CTG G GT GAG GCA TGC AGC TGC      96
Leu Leu Ala Leu Leu Arg Pro Pro Gly Leu G ly Glu Ala Cys Ser Cys
             20                  25                  30

GCC CCG GCG CAC CCT CAG CAG CAC ATC TGC C AC TCG GCA CTT GTG ATT     144
Ala Pro Ala His Pro Gln Gln His Ile Cys H is Ser Ala Leu Val Ile
         35                  40                  45

CGG GCC AAA ATC TCC AGT GAG AAG GTA GTT C CG GCC AGT GCA GAC CCT     192
Arg Ala Lys Ile Ser Ser Glu Lys Val Val P ro Ala Ser Ala Asp Pro
     50                  55                  60

GCT GAC ACT GAA AAA ATG CTC CGG TAT GAA A TC AAA CAG ATA AAG ATG     240
Ala Asp Thr Glu Lys Met Leu Arg Tyr Glu I le Lys Gln Ile Lys Met
 65                  70                  75                  80

TTC AAA GGG TTT GAG AAA GTC AAG GAT GTT C AG TAT ATC TAT ACG CCT     288
Phe Lys Gly Phe Glu Lys Val Lys Asp Val G ln Tyr Ile Tyr Thr Pro
                 85                  90                  95

TTT GAC TCT TCC CTC TGT GGT GTG AAA CTA G AA GCC AAC AGC CAG AAG     336
Phe Asp Ser Ser Leu Cys Gly Val Lys Leu G lu Ala Asn Ser Gln Lys
            100                 105                 110

CAG TAT CTC TTG ACT GGT CAG GTC CTC AGT G AT GGA AAA GTC TTC ATC     384
Gln Tyr Leu Leu Thr Gly Gln Val Leu Ser A sp Gly Lys Val Phe Ile
        115                 120                 125

CAT CTG TGC AAC TAC ATC GAG CCC TGG GAG G AC CTG TCC TTG GTG CAG     432
His Leu Cys Asn Tyr Ile Glu Pro Trp Glu A sp Leu Ser Leu Val Gln
    130                 135                 140

AGG GAA AGT CTG AAT CAT CAC TAC CAT CTG A AC TGT GGC TGC CAA ATC     480
Arg Glu Ser Leu Asn His His Tyr His Leu A sn Cys Gly Cys Gln Ile
145                 150                 155                 160

ACC ACC TGC TAC ACA GTA CCC TGT ACC ATC T CG GCC CCT AAC GAG TGC     528
Thr Thr Cys Tyr Thr Val Pro Cys Thr Ile S er Ala Pro Asn Glu Cys
                165                 170                 175

CTC TGG ACA GAC TGG CTG TTG GAA CGA AAG C TC TAT GGT TAC CAG GCT     576
Leu Trp Thr Asp Trp Leu Leu Glu Arg Lys L eu Tyr Gly Tyr Gln Ala
            180                 185                 190

CAG CAT TAT GTC TGT ATG AAG CAT GTT GAC G GC ACC TGC AGC TGG TAC     624
Gln His Tyr Val Cys Met Lys His Val Asp G ly Thr Cys Ser Trp Tyr
        195                 200                 205

CGG GGC CAC CTG CCT CTC AGG AAG GAG TTT G TT GAC ATC GTT CAG CCC     672
Arg Gly His Leu Pro Leu Arg Lys Glu Phe V al Asp Ile Val Gln Pro
    210                 215                 220

TAG                                                                  675
```

(2) INFORMATION FOR SEQ ID NO:2:

(i) SEQUENCE CHARACTERISTICS:
      (A) LENGTH: 224 amino acids
      (B) TYPE: amino acid
      (D) TOPOLOGY: linear (ii) MOLECULE TYPE: protein (xi) SEQUENCE DESCRIPTION: SEQ ID NO:2:

```
Met Pro Gly Ser Pro Arg Pro Ala Pro Ser Trp Val Leu Leu Arg
 1               5                  10                  15

Leu Leu Ala Leu Leu Arg Pro Gly Leu Gly Glu Ala Cys Ser Cys
                20                  25                  30

Ala Pro Ala His Pro Gln Gln His Ile Cys His Ser Ala Leu Val Ile
         35                  40                  45

Arg Ala Lys Ile Ser Ser Glu Lys Val Val Pro Ala Ser Ala Asp Pro
 50                  55                  60

Ala Asp Thr Glu Lys Met Leu Arg Tyr Glu Ile Lys Gln Ile Lys Met
 65                  70                  75                  80

Phe Lys Gly Phe Glu Lys Val Lys Asp Val Gln Tyr Ile Tyr Thr Pro
                 85                  90                  95

Phe Asp Ser Ser Leu Cys Gly Val Lys Leu Glu Ala Asn Ser Gln Lys
                100                 105                 110

Gln Tyr Leu Leu Thr Gly Gln Val Leu Ser Asp Gly Lys Val Phe Ile
        115                 120                 125

His Leu Cys Asn Tyr Ile Glu Pro Trp Glu Asp Leu Ser Leu Val Gln
    130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
                180                 185                 190

Gln His Tyr Val Cys Met Lys His Val Asp Gly Thr Cys Ser Trp Tyr
        195                 200                 205

Arg Gly His Leu Pro Leu Arg Lys Glu Phe Val Asp Ile Val Gln Pro
210                 215                 220
```

(2) INFORMATION FOR SEQ ID NO:3:

(i) SEQUENCE CHARACTERISTICS:
        (A) LENGTH: 218 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gly Ala Ala Ala Arg Thr Leu Arg Leu Ala Leu Gly Leu Leu Leu
 1               5                  10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
         35                  40                  45

Ala Val Ser Glu Lys Glu Val Asp Ser Gly Asn Asp Ile Tyr Gly Asn
 50                  55                  60

Pro Ile Lys Arg Ile Tyr Glu Ile Lys Ile Lys Met Phe Lys Gly Pro
65                   70                  75                  80

Glu Lys Asp Ile Glu Phe Ile Tyr Thr Ala Pro Ser Ser Ala Val Cys
                 85                  90                  95

Gly Val Ser Leu Asp Val Gly Gly Lys Lys Glu Tyr Leu Ile Ala Gly
```

```
                    100                 105                 110
Lys Ala Glu Gly Asp Gly Lys Met His Ile Thr Leu Cys Asp Phe Ile
            115                 120                 125
Val Pro Trp Asp Thr Leu Ser Thr Thr Gln Lys Lys Ser Leu Asn His
    130                 135                 140
Arg Tyr Gln Met Gly Cys Glu Cys Lys Ile Thr Arg Cys Pro Met Ile
145                 150                 155                 160
Pro Cys Tyr Ile Ser Ser Pro Asp Glu Cys Leu Trp Met Asp Trp Val
                165                 170                 175
Thr Glu Lys Asn Ile Asn Gly His Gln Ala Lys Phe Phe Ala Cys Ile
            180                 185                 190
Lys Arg Ser Asp Gly Ser Cys Ala Trp Tyr Arg Gly Ala Ala Pro Pro
        195                 200                 205
Lys Gln Glu Phe Leu Asp Ile Glu Asp Pro
    210                 215

(2) INFORMATION FOR SEQ ID NO:4:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Thr Pro Trp Leu Gly Leu Ile Val Leu Leu Gly Ser Trp Ser Leu
1               5                   10                  15
Gly Asp Trp Gly Ala Glu Ala Cys Thr Cys Ser Pro Ser His Pro Gln
            20                  25                  30
Asp Ala Phe Cys Asn Ser Asp Ile Val Ile Arg Ala Lys Val Val Gly
        35                  40                  45
Lys Lys Leu Val Lys Glu Gly Pro Phe Gly Thr Leu Val Tyr Thr Ile
    50                  55                  60
Lys Gln Met Lys Met Tyr Arg Gly Phe Thr Lys Met Pro His Val Tyr
65                  70                  75                  80
Ile His Thr Glu Ala Ser Glu Ser Leu Cys Gly Leu Lys Leu Glu Val
                85                  90                  95
Asn Lys Tyr Gln Tyr Leu Leu Thr Gly Arg Val Tyr Asp Gly Lys Met
            100                 105                 110
Tyr Thr Gly Leu Cys Asn Phe Val Glu Arg Trp Asp Gln Leu Thr Leu
        115                 120                 125
Ser Gln Arg Lys Gly Leu Asn Tyr Arg Tyr His Leu Gly Cys Asn Cys
    130                 135                 140
Lys Ile Lys Ser Cys Tyr Tyr Leu Pro Cys Phe Val Thr Ser Lys Asn
145                 150                 155                 160
Glu Cys Leu Trp Thr Asp Met Leu Ser Asn Phe Gly Tyr Pro Gly Tyr
                165                 170                 175
Gln Ser Lys His Tyr Ala Cys Ile Arg Gln Lys Gly Gly Tyr Cys Ser
            180                 185                 190
Trp Tyr Arg Gly Trp Ala Pro Pro Asp Lys Ser Ile Ile Asn Ala Thr
        195                 200                 205
Asp Pro
    210
```

(2) INFORMATION FOR SEQ ID NO:5:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Ala Pro Phe Glu Pro Leu Ala Ser Gly I le Leu Leu Leu Trp
1               5                  10                  15

Leu Ile Ala Pro Ser Arg Ala Cys Thr Cys V al Pro Pro His Pro Gln
                20                  25                  30

Thr Ala Phe Cys Asn Ser Asp Leu Val Ile A rg Ala Lys Phe Val Gly
            35                  40                  45

Thr Pro Glu Val Asn Gln Thr Thr Leu Tyr G ln Arg Tyr Glu Ile Lys
        50                  55                          60

Met Thr Lys Met Tyr Lys Gly Phe Gln Ala L eu Gly Asp Ala Ala Asp
65                  70                  75                  80

Ile Arg Phe Val Tyr Thr Pro Ala Met Glu S er Val Cys Gly Tyr Phe
                85                  90                  95

His Arg Ser His Asn Arg Ser Glu Glu Phe L eu Ile Ala Gly Lys Leu
                100                 105                 110

Gln Asp Gly Leu Leu His Ile Thr Thr Cys S er Phe Val Ala Pro Trp
            115                 120                 125

Asn Ser Leu Ser Leu Ala Gln Arg Arg Gly P he Thr Lys Thr Tyr Thr
        130                 135                 140

Val Gly Cys Glu Glu Cys Thr Val Phe Pro C ys Leu Ser Ile Pro Cys
145                 150                 155                 160

Lys Leu Gln Ser Gly Thr His Cys Leu Trp T hr Asp Gln Leu Leu Gln
                165                 170                 175

Gly Ser Glu Lys Gly Phe Gln Ser Arg His L eu Ala Cys Leu Pro Arg
            180                 185                 190

Glu Pro Gly Leu Cys Thr Trp Gln Ser Leu A rg Ser Gln Ile Ala
        195                 200                 205
```

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCCAGAGGAT CCTGCAGCTG CGCCCCGGCG CAC                                     33

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CGGCTTCTAG AACTAGGGCT GAACGATGTC AAC                              33

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCCAGAGGAT CCGCCACCAT GCCTGGGAGC CCTCGGCCC                        39

(2) INFORMATION FOR SEQ ID NO:9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGGCTTCTAG AATCAAGCGT AGTCTGGGAC GTCGTATGGG TAGGGCTGAA C GATGTCAAC    60

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCCAGAGGAT CCATGCCTGG GAGCCCTCGG CCC                              33

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGGCTTCTAG AACTAGGGCT GAACGATGTC AAC                              33
```